US006034284A

United States Patent [19]

Doi et al.

[11] Patent Number: 6,034,284

[45] Date of Patent: Mar. 7, 2000

[54] PRODUCING METHOD FOR TRIMETHYLOLALKANE

[75] Inventors: Kenji Doi; Takuhiko Jinno; Ayao Moriyama; Shingo Uji, all of Sodegaura, Japan

[73] Assignee: Koei Chemical Company, Limited, Osaka, Japan

[21] Appl. No.: 09/175,431

[22] Filed: Oct. 20, 1998

[30] Foreign Application Priority Data

| | | | |
|---|---|---|---|
| Oct. 22, 1997 | [JP] | Japan | 9-309232 |
| Nov. 11, 1997 | [JP] | Japan | 9-327059 |

[51] Int. Cl.$^{7}$ .................. C07C 31/18

[52] U.S. Cl. .................. 568/853; 568/914; 568/854

[58] Field of Search .................. 568/853, 854, 568/913

[56] References Cited

U.S. PATENT DOCUMENTS

| | | | |
|---|---|---|---|
| 4,372,833 | 2/1983 | King, Jr. | 204/157.52 |
| 4,474,959 | 10/1984 | Drury | 544/351 |
| 4,514,578 | 4/1985 | Immel et al. . | |
| 4,594,461 | 6/1986 | Merger et al. | 568/853 |
| 5,149,861 | 9/1992 | Merger | 560/234 |
| 5,334,759 | 8/1994 | Lippert | 562/609 |
| 5,763,690 | 6/1998 | Salek | 568/853 |

FOREIGN PATENT DOCUMENTS

| | | | |
|---|---|---|---|
| 1952738 | 10/1969 | Germany | C07C 31/18 |
| 1952738 | 7/1970 | Germany . | |
| 1553527 | 3/1990 | U.S.S.R. . | |
| 9717313 | 5/1997 | WIPO . | |

*Primary Examiner*—Gary Geist
*Assistant Examiner*—Jean F Vollano
*Attorney, Agent, or Firm*—Stevens, Davis, Miller & Mosher, L.L.P.

[57] ABSTRACT

High quality trimethylolalkane can be easily and efficiently produced at a high yield through a reaction between n-alkanal and formaldehyde in the presence of tertiary amine and water, in which a reaction mixture obtained after the reaction is heated up to a temperature at which a salt of tertiary amine with formic acid produced as a by-product can be thermally dissociated so as to distill tertiary amine and water from the reaction mixture, and a formate of trimethylolalkane produced in the distillation of tertiary amine and contained in a residue is reacted with water, ammonia, primary amine or secondary amine; and the tertiary amine distilled from the reaction mixture is reused in producing trimethylolalkane.

16 Claims, No Drawings

PRODUCING METHOD FOR TRIMETHYLOLALKANE

BACKGROUND OF THE INVENTION

The present invention relates to a method of producing trimethylolalkane by a reaction between n-alkanal and formaldehyde in the presence of tertiary amine and water.

Trimethylolalkane is useful as a raw material for an alkyd resin, a polyurethane resin, a (un)saturated polyester resin, a synthetic lubricating oil, a surfactant, a reactive monomer and the like.

As a known method of producing trimethylolalkane, n-alkanal is reacted with formaldehyde in the presence of a hydroxide of an alkaline metal or an alkali earth metal. In this method, alkaline metal formate or alkali earth metal formate is produced as a by-product. Trimethylolalkane is catalytically thermally decomposed by the formate. Accordingly, in conducting distillation, a general isolating and purifying technique for trimethylolalkane, it is necessary to sufficiently separate trimethylolalkane from the alkaline metal formate or the alkali earth metal formate in order to prevent the yield of trimethylolalkane from being lowered by the catalytic thermal decomposition. Thus, the separation is troublesome.

As an improvement of the aforementioned method, a method of producing trimethylolalkane by using tertiary amine and water instead of the hydroxide of an alkaline metal or an alkali earth metal has been proposed (West Germany Patent No. 1952738). In this method using tertiary amine the formate produced as a by-product is a salt of tertiary amine with formic acid, which does not catalytically thermally decompose trimethylolalkane. Therefore, the thermal decomposition of trimethylolalkane can be suppressed. In this method, the salt of tertiary amine with formic acid is separated from trimethylolalkane by utilizing a difference in the boiling points between the salt and trimethylolalkane.

However, the aforementioned improved method has the following disadvantage. In the separation of a salt of tertiary amine with formic acid from trimethylolalkane by using the difference in the boiling points therebetween, formic acid produced by thermal dissociation of the salt reacts with trimethylolalkane to produce a formate of trimethylolalkane. As a result, the yield of trimethylolalkane is lowered.

SUMMARY OF THE INVENTION

In order to overcome the aforementioned conventional disadvantage, the present invention have extensively studied a method of producing trimethylolalkane by a reaction between n-alkanal and formaldehyde in the presence of tertiary amine and water. As a result, they have found that lowering yield of trimethylolalkane due to the generation of the formate of trimethylolalkane can be prevented according to the following manner:

A reaction mixture obtained after the reaction is heated up to a temperature at which a salt of tertiary amine with formic acid produced as a by-product is thermally dissociated into formic acid and tertiary amine, so as to distill tertiary amine and water from the reaction mixture.

Then, the thus obtained residue is reacted with water, ammonia, primary amine or secondary amine. By this reaction the formate of trimethylolalkane produced during the distillation of tertiary amine and included in the residue can be easily and efficiently decomposed, and trimethylolalkane is produced.

On the basis of this finding, the present invention has been completed.

Furthermore, the tertiary amine distilled from the reaction mixture obtained after the reaction can be reused in the production of trimethylolalkane. Thus, another aspect of the invention has been completed.

The present invention provides:

(1) a method of producing trimethylolalkane through a reaction between n-alkanal and formaldehyde in the presence of tertiary amine and water, in which a reaction mixture obtained after the reaction is heated up to a temperature at which a salt of tertiary amine with formic acid produced as a by-product can be thermally dissociated so as to distill tertiary amine and water from the reaction mixture, and a formate of trimethylolalkane produced in the distillation of tertiary amine and contained in a residue is reacted with water, ammonia, primary amine or secondary amine; and (2) a method of producing trimethylolalkane, in which the tertiary amine distilled from the reaction mixture obtained after the reaction in the method (1) is reused in producing trimethylolalkane.

As described above, in the method of producing trimethylolalkane of this invention, the salt of tertiary amine with formic acid produced as a by-product is thermally dissociated and also a formate of trimethylolalkane included in the residue is decomposed. Therefore, no formate is substantially produced in this method.

According to the invention, the tertiary amine distilled from the reaction mixture obtained after the reaction can be reused in the production of trimethylolalkane.

DETAILED DESCRIPTION OF THE INVENTION

The production of trimethylolalkane in the present invention through a reaction between n-alkanal and formaldehyde in the presence of tertiary amine and water comprises (1) production of aldol through an aldol condensation reaction between n-alkanal and formaldehyde in the presence of tertiary amine, and (2) production of trimethylolalkane and a salt of tertiary amine with formic acid through a crossed Cannizzaro reaction among aldol, formaldehyde, tertiary amine and water.

After the aldol condensation reaction and the crossed Cannizzaro reaction, the resultant reaction mixture is heated up to a temperature at which the salt of tertiary amine with formic acid produced as a by-product can be thermally dissociated, thereby distilling tertiary amine and water from the reaction mixture. Through the thermal dissociation of the salt of tertiary amine with formic acid, formic acid and tertiary amine are produced. The thus produced formic acid reacts with trimethylolalkane, thereby producing a formate of trimethylolalkane.

In assuming that triethylamine and n-butanal are used as the tertiary amine and the n-alkanol, respectively, the aldol condensation reaction, the crossed Cannizzaro reaction, the thermal dissociation of the salt of tertiary amine with formic acid and the generation of the formate of trimethylolalkane in the present method are represented by the following reaction formulas:

(1) Aldol condensation reaction:

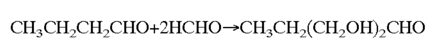

$$CH_3CH_2CH_2CHO+2HCHO \rightarrow CH_3CH_2(CH_2OH)_2CHO$$

(2) Crossed Cannizzaro reaction:

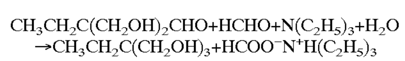

$$CH_3CH_2C(CH_2OH)_2CHO+HCHO+N(C_2H_5)_3+H_2O \rightarrow CH_3CH_2C(CH_2OH)_3+HCOO^-N^+H(C_2H_5)_3$$

(3) Thermal dissociation of the salt of tertiary amine with formic acid and generation of formate of trimethylolalkane:

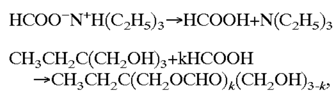

$$HCOO^-N^+H(C_2H_5)_3 \rightarrow HCOOH + N(C_2H_5)_3$$

$$CH_3CH_2C(CH_2OH)_3 + kHCOOH \rightarrow CH_3CH_2C(CH_2OCHO)_k(CH_2OH)_{3-k},$$

wherein k is 1 through 3.

The tertiary amine produced through the reaction (3) is distilled by heating the reaction mixture. The formate of trimethylolalkane produced as a by-product of the reaction (3) remains in the residue. In this invention, the formate of trimethylolalkane included in the residue is reacted with water, ammonia, primary amine or secondary amine, thereby producing trimethylolalkane.

In the case where the formate of trimethylolalkane is reacted with water, the formate of trimethylolalkane is decomposed into trimethylolalkane, and hydrogen and carbon dioxide, and/or water and carbon monoxide. In assuming that trimethylolalkane and n-butanal are used as the tertiary amine and the n-alkanal, respectively, this reaction is represented as follows:

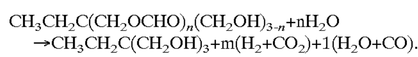

$$CH_3CH_2C(CH_2OCHO)_n(CH_2OH)_{3-n} + nH_2O \rightarrow CH_3CH_2C(CH_2OH)_3 + m(H_2 + CO_2) + 1(H_2O + CO).$$

wherein n is 1, 2 or 3, 1 and m are 0 through 3, and l+m=n.

When the formate of trimethylolalkane is reacted with ammonia, primary amine or secondary amine, trimethylolalkane and a formamide are produced. In assuming triethylamine, n-butanal and dimethylamine are used, this reaction is represented as follows:

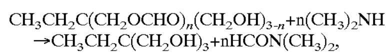

$$CH_3CH_2C(CH_2OCHO)_n(CH_2OH)_{3-n} + n(CH_3)_2NH \rightarrow CH_3CH_2C(CH_2OH)_3 + nHCON(CH_3)_2,$$

wherein n is 1, 2 or 3.

The aldol condensation reaction and the crossed Cannizzaro reaction of this invention will now be described.

Examples of the n-alkanal used in the present invention include propanal, n-butanal, n-pentanal, 3-methylbutanal, n-hexanal, 3-methylpentanal, n-heptanal, 4-methylhexanal and n-octanal.

An aqueous solution including 5 through 50% by weight formaldehyde is generally used as the formaldehyde in this invention. Preferably, 5 through 50% by weight formalin (namely, a formaldehyde aqueous solution) with a content of methanol of 1% by weight or less is used.

As the tertiary amine of this invention, a tertiary amine having a boiling point lower than the boiling point of trimethylolalkane and the boiling point of the formate of trimethylolalkane can be used. When such a tertiary amine is used, the tertiary amine can be easily distilled and recovered by heating the reaction mixture after the reaction. Examples of preferred tertiary amine include aliphatic tertiary monoamines such as trimethylamine, triethylamine, tri(n-proply)amine, triisopropylamine, tri(n-butyl)amine, triisobutylamine, diethylmethylamine, dimethylethylamine, dimethyl-n-propylamine, dimethylisopropylamine, diemthyl-n-butylamine and dimethylisobutylamine; aliphatic tertiary diamines such as triethylenediamine, N,N,N', N'-tetramethylethylenediamine and N,N,N',N'-tetramethyl-1,3-propanediamine; and nitrogen heterocyclic tertiary amines such as N-methylmorpholine, N-ethylmorpholine, N-methylpiperidine and N-ethylpiperidine. One or a combination of two or more of these tertiary amines can be used. Particularly preferably, triethylamine is used as the tertiary amine.

The mole ration of the formaldehyde to be used is preferably 3 through 4 moles, more preferably 3.2 through 3.6 moles, per 1 mole of the n-alkanal. The mole ratio of the tertiary amine to be used is preferably 1 through 2 moles, more preferably 1.1 through 1.5 moles, per 1 mole of the n-alkanal. When the mole ratio of the formaldehyde exceeds the aforementioned range, the recovery of the tertiary amine becomes difficult. Also, when the mole ratio of the tertiary amine exceeds the aforementioned range, the yield of trimethylolalkane is no longer improving, and an acid required for neutralization costs more and a longer time is required for the recovery of the tertiary amine.

The amount of water to be used is 200 through 600% by weight, and preferably 250 through 500% by weight on the basis of the total amount of the n-alkanal, the formaldehyde and the tertiary amine.

The aldol condensation reaction is conducted at −5 through 90° C., and preferably, 10 through 60° C. When the temperature is lower than −5° C., the reaction speed is very low, and when the temperature exceeds 90° C., a by-product is easily produced. The crossed Cannizzaro reaction is conducted at 20 through 90° C., and preferably, 40 through 80° C. When the temperature is lower than 20° C., the reaction requires a significantly long time, and when the temperature exceeds 90° C., a by-product other than a salt of tertiary amine with formic acid tends to be produced.

In this invention, the aldol condensation reaction and the crossed Cannizzaro reaction are successively proceeded. Therefore, more preferably, the temperature is first set at 10 through 40° C. so as to mainly proceed the aldol condensation reaction, and then set at 40 through 80° C. so as to mainly proceed the crossed Cannizzaro reaction.

After the aldol condensation reaction and the crossed Cannizzaro reaction are completed, the obtained reaction mixture is heated up to a temperature at which the salt of tertiary amine with formic acid produced as the by-product can be thermally dissociated, thereby distilling the tertiary amine and water. Preferably, the reaction mixture is ultimately heated to 120 through 190° C. in order that the salt of tertiary amine with formic acid is thermally dissociated into formic acid and tertiary amine and the tertiary amine and water can be distilled from the reaction mixture.

The heat treatment of the reaction mixture can be conducted under reduced pressure, atmospheric pressure of increased pressure. The distilled tertiary amine is reused in the production of trimethylolalkane of this invention. The distillation of the tertiary amine and water by heating the reaction mixture is conducted so as to reduce the content of water in the residue to be smaller than 20% by weight. In this manner, the tertiary amine can be recovered at a high yield. In particular, almost all water is preferably distilled for recovering the tertiary amine in a high yield. The residue obtained by distilling the tertiary amine includes the formate of trimethylolalkane produced through a reaction between trimethylolalkane and formic acid produced through the thermal dissociation.

Subsequently, the obtained residue is reacted with water, ammonia, primary amine or secondary amine.

When the residue is reacted with water, the residue is heated in the presence of water, so that the formate of trimethylolalkane included in the residue can be decomposed into trimethylolalkane, and hydrogen and carbon dioxide, and/or water and carbon monoxide. The amount of water to be used is 5 through 50 parts by weight, and preferably 7 through 30 parts by weight per 100 parts by weight of the residue. When the amount of water is smaller than this range, the formate of trimethylolalkane is difficult to decompose. When the amount exceeds the range, although there arises no specific problem in the decomposition, the usage efficiency of a vessel is poor. The amount of water can be adjusted within the aforementioned range by controlling the amount of water to be distilled in the distillation of the tertiary amine and water from the reaction mixture through the heating treatment. However, it is preferred that water is added at the aforementioned proportion to the residue obtained by distilling almost all the tertiary amine and water from the reaction mixture.

The reaction between the formate of trimethylolalkane and water can be more easily and more efficiently conducted by heating the residue under an increased pressure. In the case where no noble metal catalyst is used, the reaction is carried out generally under a pressure of 6.9 MPa (70 kgf/cm$^2$) or less, and preferably 3.4 through 5.9 MPa (35 through 60 kgf/cm$^2$) at 200 through 300° C., and preferably 210 through 280° C. In this manner, the decomposition of the formate of trimethylolalkane can be efficiently proceeded, and trimethylolalkane is produced from the formate of trimethylolalkane in a high yield.

Also, the reaction between the formate of trimethylolalkane and water can be more easily and more efficiently performed by heating the residue in the presence of a noble metal catalyst.

Examples of the noble metal catalyst include a ruthenium catalyst, a rhodium catalyst, a palladium catalyst, an osmium catalyst, a yttrium catalyst and a platinum catalyst. Among which a palladium catalyst is preferred. Alternatively, a noble metal catalyst obtained by modifying any of these noble metal catalysts with a group 14 element of the periodic table can be used. In particular, a noble metal catalyst modified with lead is preferred. One or a combination of two or more of these noble metal catalysts can be used.

Generally, a noble metal catalyst supported by a carrier, such as carbon, alumina, silica or a high molecular compound including a basic nitrogen atomic group, in an amount of 0.5 through 10% by weight is used. The form of the catalyst can be powder, grain or pellet. The suspension method or the fixed bed method is adopted for the heat treatment in the presence of the noble metal catalyst.

The amount of the noble metal catalyst to be used is 1 through 15% by weight per 100% by weight of a formic acid component (HCOOH) produced through hydrolysis of the formate of trimethylolalkane included in the residue.

Furthermore, when a solid acid catalyst is used together in the decomposition of the formate of trimethylolalkane, time required for the decomposition can be shortened. Examples of the solid acid catalyst include γ-aluminum oxide, an acid ion exchanger, natural and synthetic zeolite and heteropolyacid. One or a combination of two or more of these solid acid catalysts can be used.

The amount of the solid acid catalyst to be used is 0.1 through 5 parts by weight per 100% by weight of the formic acid component (HCOOH) produced through the hydrolysis of the formate of trimethylolalkane included in the residue.

When the noble metal catalyst is used, the reaction between the formate of trimethylolalkane and water is conducted under atmospheric pressure or an increased pressure of 1.96 MPa (20 kgf/cm$^2$) or less, preferably 0.49 through 1.47 MPa (5 through 15 kgf/cm$^2$) at 50 through 300° C., preferably 80 through 250° C. In this manner, the decomposition of the formate of trimethylolalkane can be efficiently proceeded, and trimethylolalkane is produced from the formate of trimethylolalkane in a high yield.

When the formate of trimethylolalkane included in the residue is reacted with ammonia, primary amine or secondary amine, the residue is mixed and reacted with ammonia, primary amine or secondary amine, thereby producing trimethylolalkane and a formamide.

As the primary amine and the secondary amine, a compound including, in its molecule, at least one nitrogen atom bonded with one or two hydrogen atoms can be used. Preferably, primary monoamine and secondary monoamine including, in their molecules, one nitrogen atom bonded with one or two hydrogen atoms are used. As the ammonia, the primary amine and the secondary amine reacted with the formate of trimethylolalkane, ammonia, primary monoamine and secondary monoamine are preferred.

Examples of the primary monoamine include aliphatic primary monoamines such as methylamine, ethylamine, n-propylamine, isopropylamine, n-butylamine, isobutylamine, n-pentylamine, isopentylamine, neopentylamine, n-hexylamine, 2-methylpentylamine, 3-methylpentylamine, 2,2-dimethylbutylamine and 2,3-dimethylbutylamine; alicyclic primary monoamines such as cyclopropylamine, cyclobutylamine, cyclopentylamine, cyclohexylamine and any of these alicyclic amines including, in the ring, a carbon atom bonded with an aliphatic hydrocarbon group such as a methyl group, an ethyl group, an n-propyl group, an isopropyl group, an n-butyl group and an isobutyl group; and aromatic primary monoamines such as aniline, benzylamine, α-phenethylamine, β-phenethylamine, and any of these aromatic amines wherein the benzene ring is bonded with an aliphatic hydrocarbon group, such as a methyl group, an ethyl group, an n-propyl group, an isopropyl group, an n-butyl group and an isobutyl group.

Examples of the secondary monoamine include amine obtained by substituting a hydrogen atom bonded with a nitrogen atom of any of the aforementioned primary monoamines with an aliphatic hydrocarbon group such as a methyl group, an ethyl group, an n-propyl group, an isopropyl group, an n-butyl group, an isobutyl group, an n-pentyl group and an n-hexyl group. Specifically, examples of the secondary monoamine include aliphatic secondary monoamines such as dimethylamine, diethylamine, di(n-propyl)amine, diisopropylamine, di(n-butyl)amine, diisobutylamine, di(n-pentyl)amine and di(n-hexyl)amine; alicyclic secondary monoamines such as N-methylcyclopropylamine, N-ethylcyclopropylamine, N-methylcyclobutylamine, N-ethylcyclobutylamine, N-methylcyclopentylamine, N-ethylcyclopentylamine, N-methycyclohexylamine and N-ethylcyclohexylamine; aromatic secondary monoamines such as N-methylaniline, N-ethylaniline, N-methylbenzylamine, N-ethylbenzylamine, N-methyl-α-phenethylamine, N-ethyl-α-phenethylamine, N-methyl-β-phenethylamine and N-ethyl-β-phenethylamine; and nitrogen containing cyclic secondary monoamines such as pyrrolidine, piperidine, homopiperidine, morpholine, and a compound including an aliphatic hydrocarbon group, such as a methyl group, an ethyl group, an n-propyl group, an isopropyl group, an n-butyl group and an isobutyl group, bonded with a carbon atom in the ring of any of these nitrogen cyclic amines.

The amount of the ammonia, the primary amine or the secondary amine to be used is 1 mole or more, preferably 1.1 through 2.0 moles, per 1 mole of the formic acid component included in the formate of trimethylolalkane. When the amount of the ammonia, the primary amine or the secondary amine is smaller than this range, the formate of trimethylolalkane remains in the residue.

The reaction between the formate of trimethylolalkane included in the residue and the ammonia, the primary amine or the secondary amine is conducted at a temperature of room temperature or more, and preferably at a temperature ranging between room temperature and 130° C., under atmospheric pressure, reduced pressure or increased pressure. This reaction is an exothermic reaction. Hence, the ammonia, the primary amine or the secondary amine is preferably added dropwise to the residue while keeping the aforementioned temperature with stirring the residue. The ammonia, the primary amine or the secondary amine can be dissolved in a solvent to be mixed with the residue, and the solvent is preferably water.

The method of this invention can be carried out by a batch method or a continuous method. Now, a preferred embodiment of the invention adopting the batch method will be described.

While keeping a mixture of formaldehyde (3.2 through 3.6 moles per 1 mole of n-alkanal) and water (250 through 500% by weight based on a total amount of n-alkanal, formaldehyde and tertiary amine) charged in a reactor at 10 through 40° C., n-alkanal and tertiary amine (1 through 1.5 mole per 1 mole of n-alkanal) are supplied to the reactor over 1 through 3 hours. Subsequently, contents of the reactor is kept at 40 through 60° C. for 1 through 3 hours for completing the aldol condensation reaction, and, then, is kept at 60 through 80° C. for 1 through 2 hours for completing the crossed Cannizzaro reaction.

After completing these reactions, the reaction mixture is treated with a copper oxide catalyst at 60 through 80° C. for 1 through 4 hours, with tertiary amine added if necessary, so that excessive formaldehyde can be changed into methanol and a salt of tertiary amine with formic acid. The amount of the copper oxide catalyst to be used is 0.5 through 5% by weight, and preferably 1 through 3% by weight of the reaction mixture.

After the treatment with the copper oxide catalyst, excessive tertiary amine is neutralized with formic acid, and methanol and water are distilled from the reaction mixture under reduced pressure. Then, after distilling almost all water, tertiary amine is distilled and recovered as an azeotropic mixture with water. The distillation of methanol, water and tertiary amine is conducted by heating the reaction mixture up to 120 through 190° C. ultimately. The mixture of tertiary amine and water recovered as the azeotropic mixture is reused as it is in the reaction system, or tertiary amine in the mixture is separated from water so as to be reused in the reaction system.

In producing trimethylolalkane through the reaction between the formate of trimethylolalkane and water without using a noble metal catalyst, after distilling tertiary amine, 5 through 50 parts by weight of water is added per 100 parts by weight of the residue. The resultant residue is heated to 210 through 280° C. under a pressure of 3.4 through 5.9 MPa (35 through 60 kgf/cm$^2$), so as to decompose the formate of trimethylolalkane into trimethylolalkane, and hydrogen and carbon dioxide, and/or water and carbon monoxide. The hydrogen and carbon dioxide and/or water and carbon monoxide are removed from the system.

In producing trimethylolalkane through the reaction between the formate of trimethylolalkane and water by using a noble metal catalyst, after distilling tertiary amine, 5 through 50 parts by weight of water is added per 100 parts by weight of the residue. Then, a noble catalyst, and a solid acid catalyst if necessary, are further added. The resultant residue is heated to 80 through 250° C. under a pressure of 0.49 through 1.47 MPa (5 through 15 kgf/cm$^2$), so as to decompose the formate of trimethylolalkane into trimethylolalkane, and hydrogen and carbon dioxide, and/or water and carbon monoxide. The hydrogen and carbon dioxide and/or water and carbon monoxide are removed from the system.

After the formate of trimethylolalkane is decomposed and hydrogen and carbon dioxide and/or water and carbon monoxide are removed from the system, the resultant residue is filtered and distilled. Thus, trimethylolalkane with high quality can be easily isolated.

When the formate of trimethylolalkane is reacted with ammonia, primary amine or secondary amine so as to produce trimethylolalkane and a formamide, after distilling tertiary amine from the residue, the ammonia, the primary amine or the secondary amine (1 mole or more per 1 mole of the formic acid component included in the formate of trimethylolalkane) is added dropwise to the residue, with stirring, at a temperature ranging between room temperature and 130° C. Thus, the formate of trimethylolalkane in the residue can be reacted with the ammonia, the primary amine or the secondary amine, thereby producing trimethylolalkane and a formamide.

Trimethylolalkane and the formamide are separately recovered from the obtained reaction mixture through distillation or the like.

Now, preferred embodiments of the invention will be described, which do not limit the invention but merely exemplify the invention.

EXAMPLE 1

A reactor with a capacity of 5 liters equipped with a thermometer, a reflux condenser, a stirrer and a dropping funnel is charged with 3822.4 g of a 7% aqueous solution of formaldehyde (including 8.91 moles of formaldehyde). While keeping the inner temperature of the reactor at 20° C., 194.7 g (2.70 moles) of n-butanal and 303.6 g (3.00 moles) of triethylamine are added dropwise from separate dropping funnels over 1.5 hours, with stirring. Subsequently, the temperature is increased to 40° C., and the reaction is allowed to proceed for 1.5 hours. Then, the temperature is increased to 60° C. and the reaction is allowed to proceed for 1 hour, and the temperature is increased again to 80° C. and the reaction is allowed to proceed for another 1 hour. After the reaction, 100 g of a copper oxide catalyst is added, and 53.5 g (0.53 mole) of triethylamine is further added to the reaction mixture. The resultant mixture is stirred for 2 hours at 70° C., thereby treating excessive formaldehyde. The resultant reaction mixture is filtered so as to remove the copper oxide catalyst, and is adjusted to pH 5 by adding 14.0 g of formic acid. From 4388.2 g of the reaction mixture with pH adjusted, 17.9 g of methanol and 360 g of water are distilled at 60° C. under reduced pressure of 18.66 kPa (140 mmHg). Then, At 80° C. under reduced pressure of 33.32 kPa (250 mmHg), 720 g of water is distilled, and furthermore, at 180° C. under atmospheric pressure, 355 g (3.51 moles) of triethylamine is distilled and recovered as a mixture with 2470 g of water. Subsequently, 80 g of water is added to 465.3 g of the thus obtained residue, and the resultant mixture is heated to 280° C. for 2.5 hours under an increased pressure of 4.9 MPa (50 kgf/cm$^2$). Thus, a formate of trimethylolalkane included in the residue is decomposed into trimethylolpropane, and hydrogen, carbon dioxide, water and carbon monoxide. Then, hydrogen, carbon dioxide, water and carbon monoxide are removed from the reaction system to give 440 g of the residue. The obtained residue includes neither formic acid nor the formate of trimethylolpropane. From the residue, 75.5 g of water is distilled at 80° C. under reduced pressure of 33.32 kPa (250 mmHg). Then, under reduced pressure of 0.4 kPa (3 mmHg), 311 g (2.32 moles) of trimethylolpropane is distilled. The yield based on n-butanal is 86%.

EXAMPLE 2

Triethylamine is separated from the mixture of triethylamine and water recovered in Example 1 at 40°C. Trimethylolpropane is produced by using 151.8 g (1.50 moles) of the separated triethylamine according to the same manner as described in Example 1 except that the scale of the reaction is halved. As a result, 152 g (1.13 moles) of trimethylolpropane is obtained. The yield on the basis of n-butanal is 84%. The residue obtained after the decomposition of the formate of trimethylolpropane includes neither formic acid nor the formate of trimethylolpropane.

Comparative Example 1

According to the same manner as described in Example 1, a reaction mixture adjusted to pH 5 is obtained. From 4388 g of the reaction mixture, 18 g of methanol and 375 g of water is distilled at 60° C. under reduced pressure of 18.66 kPa (140 mmHg). Then, at 80° C. under reduced pressure of 33.32 kPa (250 mmHg), 828 g of water is distilled, and at 50° C. under reduced pressure of 7.33 kPa (55 mmHg), 2301 g of water, 71 g (0.70 mole) of triethylamine and 364 g (2.47 moles) of the salt of triethylamine with formic acid are distilled. Then, 429 g of the resultant residue, which includes 266 g (1.98 moles) of trimethylolpropane (with a yield on the basis of n-butanal of 73%), 110 g of the formate of trimethylolpropane (including 104 g (0.64 moles) of monoester, 6 g (0.03 mole) of diester and a trace amount of triester, and 52 g (0.35 moles) of the salt of triethylamine with formic acid), is distilled under reduced pressure of 0.4 kPa (3 mmHg) to obtain 150 g of the formate of trimethylolpropane (including 133 g (0.82 mole) of monoester, 8 g (0.04 mole) of diester and a trace amount of triester) and 246 g (1.83 mole) of trimethylolpropane (with a yield on the basis of n-butanal of 68%).

Example 3

According to the same manner as described in Example 1, a reaction mixture adjusted to pH 5 is obtained. From 4388.2 g of the reaction mixture, 17.9 g of methanol and 360 g of water are distilled at 60° C. under reduced pressure of 18.66 kPa (140 mmHg). Subsequently, at 80° C. under reduced pressure of 33.32 kPa (250 mmHg), 720 g of water is distilled. Thereafter, at 180° C. under atmospheric pressure, 355 g (3.51 moles) of triethylamine is distilled and recovered as a mixture with 2470 g of water. Subsequently, 72 g of water and 16 g of 5% palladium/carbon powder (with a 50% moisture content) are added to 465.3 g of the thus obtained residue. The resultant mixture is heated to 200° C. under an increased pressure of 0.98 MPa (10 kgf/cm$^2$) for 2.5 hours, thereby decomposing the formate of trimethylolpropane included in the residue into trimethylolpropane, hydrogen, carbon dioxide, water and carbon monoxide. Then, hydrogen, carbon dioxide, water and carbon monoxide are removed from the reaction system. Thereafter, 450 g of the resultant residue is filtered, so as to obtain 438 g of a filtrate, which includes neither formic acid nor the formate of trimethylolpropane. From the obtained filtrate, at 80° C. under reduced pressure of 33.32 kPa (250 mmHg), 73.5 g of water is distilled. Subsequently, through distillation under reduced pressure of 0.4 kPa (3 mmHg), 311 g (2.32 moles) of trimethylolpropane is obtained. The yield on the basis of n-butanal is 86%.

EXAMPLE 4

According to the same manner as described in Example 3 except that 16 g of 5% palladium/carbon powder (with a 50% moisture content) is replaced with 16 g of 5% palladium-1% lead/carbon powder (with a 50% moisture content), 311 g (2.32 moles) of trimethylolpropane is ultimately obtained. The yield on the basis of n-butanal is 86%. The decomposition of the formate of trimethylolpropane is completed in 0.5 hour, and the resultant residue includes neither formic acid nor the formate of trimethylolpropane.

EXAMPLE 5

According to the same manner as described in Example 3 except that 16 g of 5% palladium/carbon powder (with a 50% moisture content) is replaced with 16 g of 2% palladium/carbon powder (with a 50% moisture content) and 5 g of a silica-alumina catalyst (N-631HN; manufactured by JGC Corporation), 311 g (2.32 moles) of trimethylolpropane is ultimately obtained. The yield on the basis of n-butanal is 86%. The decomposition of the formate of trimethylolpropane is completed in 2.0 hours, and the resultant residue includes neither formic acid nor the formate of trimethylolpropane.

EXAMPLE 6

Triethylamine is separated from the mixture of triethylamine and water recovered in Example 3 at 40° C. Then, trimethylolpropane is produced by using 151.8 g (1.50 moles) of the thus separated triethylamine in the same manner as described in Example 3 except that the scale of the reaction is halved. As a result, 152 g (1.13 moles) of trimethylolpropane is obtained. The yield on the basis of n-butanal is 84%. The residue obtained after the decomposition of the formate of trimethylolpropane includes neither formic acid nor the formate of trimethylolpropane.

EXAMPLE 7

According to the same manner as described in Example 1, a reaction mixture adjusted to pH 5 is obtained. From 4388.2 g of the reaction mixture, at 60° C. under reduced pressure of 18.66 kPa (140 mmHg), 17.9 g of methanol and 360 g of water are distilled. Subsequently, at 80° C. under reduced pressure of 33.32 kPa (250 mmHg), 720 g of water is distilled. Thereafter, at 180° C. under atmospheric pressure, 355 g (3.51 moles) of triethylamine is distilled and recovered as a mixture with 2470 g of water. Then, 370.2 g of a 47% by weight diemthylamine aqueous solution (including 3.86 moles of dimethylamine) is added dropwise over 1 hour to 465.3 of the thus obtained residue with stirring and with keeping at 50° C. or less, so as to proceed the reaction. Then, the same temperature is further kept for another 1 hour, and the reaction is then completed. After the reaction is completed, the resultant reaction mixture includes neither formic acid nor the formate of trimethylolpropane. From 835.5 g of the thus obtained reaction mixture, at 120° C. under atmospheric pressue of 101.3 kPa (760 mmHg), 196 g of water and 16 g of dimethylamine are distilled. Then, at 80° C. under reduced pressure of 4 kPa (30 mmHg), 256 g of N,N-dimethylformamide is distilled. From the thus obtained residue, 315 g (2.35 moles) of trimethylolpropane is obtained through distillation under reduced pressure of 0.4 kPa (3 mmHg). The yield on the basis of n-butanal is 87%.

EXAMPLE 8

Triethylamine is separated from the mixture of triethylamine and water recovered in Example 7 at 40° C. Then, trimethylolpropane is produced by using 151.8 g (1.50 moles) of the thus separated triethylamine according to the same manner as described in Example 7 except that the scale of the reaction is halved. As a result, 156 g (1.16 moles) of trimethylolpropane is obtained. The yield on the basis of n-butanal is 86%. The reaction mixture obtained after the reaction with dimethylamine includes neither formic acid nor the formate of trimethylolpropane.

EXAMPLE 9

Trimethylolpropane is produced according to the same manner as described in Example 7 except that 328.1 g (3.86 moles) of piperidine is used instead of dimethylamine. The reaction mixture obtained after the reaction with piperidine includes neither formic acid nor the formate of trimethylolpropane. From 793.4 g of the thus obtained reaction mixture, at 120° C. under atmospheric pressure of 101.3 kPa (760 mmHg), 30.5 g of piperidine is distilled. Then, at 120° C. under reduced pressure of 4 kPa (30 mmHg), 395.7 g of N-formylpiperidine is distilled. Thereafter, through distillation under reduced pressure of 0.4 kPa (3 mmHg), 311 g (2.32 moles) of trimethylolpropane is obtained from the resultant residue. The yield of the basis of n-butanal is 86%.

EXAMPLE 10

Trimethylolpropane is produced according to the same manner as described in Example 7 except that 234.8 g of a 28% by weight ammonia aqueous solution (including 3.86 moles of ammonia) is used instead of dimethylamine. The reaction mixture obtained after the reaction with the ammonia aqueous solution includes neither formic acid nor the formate of trimethylolpropane. From 700.1 g of the thus obtained reaction mixture, at 120° C. under atmospheric pressure of 101.3 kPa (760 mmHg), 169 g of water and 6 g of ammonia are distilled. Then, at 120° C. under reduced pressure of 4 kPa (30 mmHg), 158 g of formamide is distilled. From the thus obtained residue, 315 g (2.35 moles) of trimethylolpropane is obtained through distillation under reduced pressure of 0.4 kPa (3 mmHg). The yield on the basis of n-butanal is 87%.

According to the method of producing trimethylolpropane of this invention, high quality trimethylolpropane can be easily and efficiently produced at a high yield because lowering of the yield of trimethylolalkane due to generation of a formate of trimethylolalkane is avoided. Also advantageously, tertiary amine can be recovered and the recovered tertiary amine can be reused in the production of trimethylolalkane. Thus, the method of producing trimethylolalkane of this invention is a very effective industrial method with remarkable advantages to the conventional techniques.

What is claimed is:

1. A method of producing a trimethylolalkane which comprises a step of reacting an n-alkanal with formaldehyde in the presence of a tertiary amine and water; a step of heating the reaction mixture thus obtained up to a temperature at which a salt of tertiary amine with formic acid produced as a by-product is thermally dissociated and the tertiary amine and water are distilled, whereby a formate of trimethylolalkane is produced and included in the residue, and a step of heating the formate of trimethylolalkane thus produced in the presence of water to decompose it, or reacting the formate of trimethylolalkane with ammonia, a primary amine or a secondary amine.

2. The method of producing a trimethylolalkane according to claim 1, wherein the step of heating the formate of trimethylolalkane is conducted in the presence of water, so as to decompose the formate of trimethylolalkane into at least one of hydrogen, carbon monoxide and trimethylolalkane, or into water and carbon monoxide and trimethylolalkane.

3. The method of producing a trimethylolalkane according to claim 2, wherein the step of heating the formate of trimethylolalkane is conducted under an increased pressure of 6.9 MPa or less.

4. The method of producing a trimethylolalkane according to claim 3, wherein the step of heating the formate of trimethylolalkane is conducted at 200 through 300° C.

5. The method of producing a trimethylolalkane according to claim 2, wherein the step of heating the formate of trimethylolalkane is conducted in the presence of a noble metal catalyst.

6. The method of producing trimethylolalkane according to claim 5, wherein the noble metal catalyst is a palladium catalyst.

7. The method of producing trimethylolalkane according to claim 5, wherein the noble metal catalyst is modified with lead.

8. The method of producing trimethylolalkane according to claim 6, wherein the palladium catalyst is modified with lead.

9. The method of producing trimethylolalkane according to claim 5, wherein the formate of trimethylolalkane is reacted with water in the presence of a solid acid catalyst.

10. The method of producing a trimethylolalkane according to claim 5, wherein the step of heating the formate of trimethylolalkane is conducted under atmospheric pressure of an increased pressure of 1.96 MPa or less.

11. The method of producing a trimethylolalkane according to claim 10, wherein the step of heating the formate of trimethylolalkane is conducted at 50 through 300° C.

12. The method of producing a trimethylolalkane according to claim 2, wherein 5 to 50 parts by weight of water is added to the residue, obtained after the distillation of the tertiary amine and water, per 100 parts by weight of the residue.

13. The method of producing trimethylolalkane according to claim 1, wherein the formate of trimethylolalkane included in the residue is reacted with ammonia, primary amine or secondary amine, so as to produce trimethylolalkane and a formamide.

14. The method of producing a trimethylolalkane according to claim 13, wherein the primary amine or the secondary amine is a primary monoamine or a secondary monoamine.

15. The method of producing trimethylolalkane according to claim 1, wherein the tertiary amine distilled from the reaction mixture is reused in a production of trimethylolalkane.

16. The method of producing trimethylolalkane according to claim 1, wherein the tertiary amine is triethylamine.

* * * * *